United States Patent [19]

Evans

[11] 4,043,870
[45] Aug. 23, 1977

[54] PROCESS OF PURIFYING CHOLESTEROL OXIDASE
[75] Inventor: Timothy W. Evans, Portage, Mich.
[73] Assignee: The Upjohn Company, Kalamazoo, Mich.
[21] Appl. No.: 685,489
[22] Filed: May 11, 1976
[51] Int. Cl.$^2$ .......................................... C07G 7/028
[52] U.S. Cl. .................................................. 195/66 R
[58] Field of Search ................. 195/66 R, 66 A, 66 B; 210/21

[56] References Cited

U.S. PATENT DOCUMENTS 3,247,104  4/1966  Sako et al. ............................ 210/21
3,907,642  9/1975  Richmond ............................. 195/62

FOREIGN PATENT DOCUMENTS 1,391,876  4/1975  United Kingdom ............. 195/66 R Primary Examiner—Lionel M. Shapiro
Attorney, Agent, or Firm—William G. Jameson; Sidney B. Williams, Jr.

[57] ABSTRACT

This invention relates to a novel process for purifying aqueous solutions which contain cholesterol oxidase. In particular, this invention relates to a process for removing nonionic surfactants from aqueous processing solutions containing cholesterol oxidase by extraction with a water-immiscible solvent.

38 Claims, No Drawings

PROCESS OF PURIFYING CHOLESTEROL OXIDASE

BACKGROUND OF THE INVENTION

The extraction of cholesterol oxidase from cholesterol oxidase producing microorganisms utilizing nonionic surfactants is well known in the art.

The extraction of cholesterol oxidase produced by various microorganisms utilizing aqueous nonionic surfactant solutions is described, inter alia, in U.S. Pat. Nos. 3,907,642 and 3,909,359 as well as British Pat. Nos. 1,385,319 and 1,391,876.

Anionic exchangers, well known and utilized in the art, do not produce a cholesterol oxidase preparation substantially free of the nonionic surfactants utilized in the extraction of cholesterol oxidase from microorganisms.

Ammonium sulfate precipitation of cholesterol oxidase from an aqueous processing solution, well known and utilized in the art, does not result in a cholesterol oxidase preparation substantially free of the nonionic surfactants utilized in the extraction of cholesterol oxidase from microorganisms.

The level of surfactant present in a cholesterol oxidase preparation affects the calibration of a cholesterol assay utilizing cholesterol oxidase bacause a given amount of surfactant is added to the assay mixture in order to solubilize the cholesterol and facilitate the binding of cholesterol to cholesterol oxidase. If excessive surfactant is present in the cholesterol oxidase preparation, the rate of binding of cholesterol to cholesterol oxidase is not reproducible from lot to lot of the cholesterol oxidase preparation, thus making calibration of a cholesterol assay difficult.

In a cholesterol assay utilizing a immobilized cholesterol oxidase preparation, the use of a cholesterol oxidase preparation (substantially free of surfactant) would be advantageous because of decreased surfactant interference with the immobilization of cholesterol oxidase.

A cholesterol oxidase preparation which is substantially free of nonionic surfactant can be further purified, if desired, more easily than a cholesterol oxidase preparation containing excessive surfactant.

BRIEF SUMMARY OF THE INVENTION

Nonionic surfactants are often utilized in the isolation of cholesterol oxidase produced by microorganisms. The subject invention relates to a process for removing nonionic surfactants from aqueous processing solutions containing cholesterol oxidase by extraction with a water-immiscible solvent.

The process of the subject invention comprises contacting an aqueous processing solution containing cholesterol oxidase with a water-immiscible solvent and precipitating the cholesterol oxidase from solution. The nonionic surfactant is extracted into the water-immiscible solvent and the cholesterol oxidase is precipitated from solution by the addition of a salt such as ammonium sulfate. The cholesterol oxidase is then collected by conventional procedures.

The term "water-immiscible solvent" as used throughout the specification and claims means, unless otherwise indicated, any water-immiscible solvent with a water solubility of greater than 1% v/v, for example n-butanol and methylene chloride.

The term "water-immiscible solvent having a water solubility of greater than 5% v/v" means any water-immiscible solvent with a water solubility of greater than 5% v/v, for example n-butanol.

The term "nonionic surfactant" as used throughout the specification and claims means any nonionic surfactant which can be utilized in the extraction of cholesterol oxidase from cholesterol oxidase producing microorganisms, including for example, modified polyethoxylated alcohol (Triton DF-18), octyl phenoxy polyethoxy ethanols, and the like. Additional nonionic surfactants utilized in the extraction of cholesterol oxidase from cholesterol oxidase producing microorganisms include the alkyl aryl ethylene glycols and polyethylene oxide-polypropylene oxide adducts, and the esters thereof (see British Pat. No. 1,391,876), as well as the polyethylene glycols.

DETAILED DESCRIPTION OF THE INVENTION

The novel process of this invention is useful for separating nonionic surfactants from aqueous processing solutions containing the enzyme cholesterol oxidase and is carried out according to the following procedures.

PROCESS A

The novel process of this invention is useful in the extraction of nonionic surfactants from aqueous solutions containing cholesterol oxidase.

Cholesterol oxidase can be produced and extracted from various microorganisms by the use of an aqueous solution of a nonionic surfactant according to principles already known in the art, for instance as given in U.S. Pat. Nos. 3,907,642 and 3,909,359 as well as British Pat. Nos. 1,385,319 and 1,391,876.

The cholesterol oxidase is recovered in the aqueous processing solution by removing the cells, for example by filtration or centrifugation; and the cholesterol oxidase is isolated from the aqueous processing solution by methods known in the art including ion exchanges and precipitation with salts, such as ammonium sulfate.

The process of the subject invention comprises the removal of the nonionic surfactant from the aqueous processing solution or a filtrate containing cholesterol oxidase, by contacting said aqueous processing solution or filtrate with a water-immiscible solvent and precipitating the cholesterol oxidase with a salt. A preferred water-immiscible solvent for the extraction of a nonionic surfactant from an aqueous process solution or filtrate containing cholesterol oxidase is n-butanol.

Suitable salts for the precipitation of cholesterol oxidase are known in the art and include ammonium sulfate, magnesium sulfate, sodium sulfate, potassium sulfate and the like.

The amount of water-immiscible solvent employed for the extraction depends, to a certain extent, upon the particular solvent employed and the surfactant to be removed and can be determined by a person skilled in the art without undue experimentation. Generally speaking, the amount of water-immiscible solvent which is added to an aqueous processing solution can be varied from about 0.1 volume per volume of aqueous processing solution to any volume in excess thereof, preferably from about 0.1 to about 2.0 volumes per volume of aqueous processing solution.

The extraction of a nonionic surfactant by the process of the subject invention can be effected at any temperature less than about 25° C. but above the freezing point of the solutions, preferably between about −5° and 5° C. The pH of the aqueous processing solution can be between 2 and 12, preferably between 4 and 10. The temperature of the water-immiscible solvent is adjusted to the desired temperature, and the aqueous processing solution/water-immiscible solvent mixture maintained at the desired temperature throughout the process extracting the nonionic surfactant and precipitation of the cholesterol oxidase.

The "contacting" of the water-immiscible solvent and the aqueous processing solution can be carried out by simply agitating the two fractions together for a period of time sufficient to extract nonionic surfactant from the aqueous process solution. The precipitation of cholesterol oxidase with an effective amount of a salt, is carried out concurrently with the contacting of the water-immiscible solvent and the aqueous processing solution. The amount of contact time can be determined by a person skilled in the art without undue experimentation, generally speaking, the contact time is between about 15 and about 60 minutes.

The precipitate of cholesterol oxidase can be recovered according to conventional methods substantially free of nonionic surfactants.

In addition, the process can be carried out upon a precipitate of cholesterol oxidase by contacting the precipitate with a water-immiscible solvent and then reisolating the cholesterol oxidase so as to obtain a cholesterol oxidase preparation substantially free of nonionic surfactants.

The amount of water-immiscible solvent which is added to a precipitate of cholesterol oxidase can be varied from about 3 volumes/weight to any volume in excess thereof, preferably from about 3 to about 100 volumes per weight of precipitate, e.g. 100 grams of cholesterol oxidase precipitate can be extracted with from about 300 ml. to about 10 liters of a water-immiscible solvent.

The "contacting" of the water-immiscible solvent and a precipitate of cholesterol oxidase can be carried out by simply agitating the two fractions together for a period of time sufficient to extract the nonionic surfactant from the precipitate of cholesterol oxidase into the water-immiscible solvent. The amount of contact time can be determined by a person skilled in the art without undue experimentation, generally speaking, the contact time is between about 15 and about 60 minutes.

Upon removal of the nonionic surfactant from the precipitate of cholesterol oxidase, the cholesterol oxidase can be recovered according to conventional methods substantially free of nonionic surfactants.

PROCESS B

An alternate process of this invention for separating nonionic surfactants from aqueous process solutions containing cholesterol oxidase, comprises contacting said aqueous process solution with a water-immiscible solvent having a water solubility of greater than 5% v/v, for example n-butanol.

The amount of water-immiscible solvent employed for the extraction depends, to a certain extent, upon the particular solvent employed and the nonionic surfactant to be removed and can be determined by a person skilled in the art without undue experimentation. Generally speaking, the amount of water-immiscible solvent having a water-solubility of greater than 5% v/v which is added to an aqueous processing solution can be varied from about 0.1 volume per volume of aqueous processing solution to any volume in excess thereof, preferably from about 0.1 to about 2.0 volumes per volume of aqueous processing solution.

The extraction of a nonionic surfactant by this procedure can be effected at any temperature less than about 25° C. but above the freezing point of the solutions, preferably between about −5° and 5° C. The pH of the aqueous processing solution can be between 2 and 12, preferably between 4 and 10. The temperature of the water-immiscible solvent is adjusted to the desired temperature, and the aqueous processing solution/water-immiscible solvent mixture maintained at the desired temperature throughout the process extracting the nonionic surfactant.

The process of the subject invention can be carried out upon an aqueous process solution prior to isolation of the enzyme from the aqueous process solution by precipitation with salt, such as ammonium sulfate, magnesium sulfate, sodium sulfate, potassium sulfate and the like.

The "contacting" of the water-immiscible solvent and an aqueous processing solution can be carried out by simply agitating the two fractions together for a period of time sufficient to extract the nonionic surfactant from the aqueous processing solution into the water-immiscible solvent having a water solubility of greater than 5% v/v. The amount of contact time can be determined by a person skilled in the art without undue experimentation, generally speaking, the contact time is between about 15 and about 60 minutes.

Upon removal of the nonionic surfactant from the aqueous process solution, the cholesterol oxidase can be recovered according to conventional methods substantially free of nonionic surfactants.

The following examples are illustrative of the present invention but are not to be construed as limiting.

The surfactant, Triton X-100; the filter aids Celaton FW-6 and Standard Supercell; and the Tris-Cl buffer utilized in the following examples are only illustrative of suitable agents which can be utilized in the extraction and isolation of a cholesterol oxidase preparation from microorganisms.

Triton X-100 (Rohm and Haas Co.) is the tradename for iso-octylphenoxypolyethoxyethanol containing approximately 10 moles, i.e. 10 polymerised units, of ethylene oxide.

Celaton FW-6 (Eagle-Picher Industries, Inc.) is the tradename for a diatomaceous earth filter aid.

Standard Supercell (Johns-Manville) is the tradename for a diatomaceous earth filter aid.

10 mM TRIS-CL BUFFER

One thousand five hundred liters of a 10 mM Tris-Cl Buffer (pH 8.0) is prepared as follows:

| | | |
|---|---|---|
| THAM (TROMETHAMINE) | 1.81 | kg. |
| Deionized Water, q.s. | 150 | liters | adjust pH to 8.0 with HCl and then dilute to 1500 liters with deionized water.

EXAMPLE 1

Five thousand liters of fermentation beer produced by bacteria in accordance with U.S. Pat. No. 3,909,359, is worked up as follows:

STEP 1

Filtration

Add 1% wt./vol. Standard Supercell as admix to beer, and using a rotary vacuum filter (Feinc), precoated with Celaton FW-6, filter the beer. Very gently agitate the beer plus filter aid during filtration.

STEP 2

Enzyme Release and Second Filtration

Combine cake from filtration (Step 1) with a surfactant solution composed of 750 liters of deionized water and 7.5 kg. of Triton X-100. Agitate for one hour. Precoat filter press with 50 kg. of Celaton FW-6, then filter and collect filtrate. Wash cake with 500 liters of deionized water in a single pass, combine with filtrate.

STEP 3

Ammonium Sulfate Precipitation

Add 200 gms. of $(NH_4)_2SO_4$ per liter of filtrate plus wash and gently agitate at 5° C. overnight. In the morning add 0.5% wt./vol. Standard Supercell and filter on a press precoated with 0.5% wt./vol. of Celaton FW-6. Be certain mother liquor is clear before proceeding. Wash cake with 30% vol./vol. (filtrate plus wash) of 200 gm./liter of $(NH_4)_2SO_4$; single pass. Be certain wash is clean before proceeding. Carefully wash precipitation vessel with 300 liters of 10 mM Tris-Cl buffer (pH 8.0), using wash to leach press. Recycle wash through filter cake for 30 minutes and collect. Wash cake with 150 liters of 10 mM Tris-Cl buffer (pH 8.0); single pass and combine with wash.

STEP 4

Surfactant Extraction and Ammonium Sulfate Precipitation

Precool 10 mM Tris-Cl buffer (pH 8.0) washings of Step 3° to 0° C. Precool 450 liters of $H_2O$ saturated n-butanol to 0° C. and combine with precooled washings, maintaining temperature at 0° C. and begin agitation. Add 100 gm. of $(NH_4)_2SO_4$ per liter of buffer solution, agitate for 30 minutes. Add 10 gm. of Standard Supercell as admix per liter of buffer solution and allow to settle for 30 minutes.

Filter on press with 10 gm. of Celaton FW-6 per liter of buffer solution as precoat. Blow press dry. (Be certain butanol and aqueous phases contain no prcipitate before processing). Wash cake with 100 liters of $H_2O$ saturated n-butanol, precooled to 0° C.; single pass (be certain wash contains no precipitate). Blow press dry. Elute press with 900 liters of 10 mM Tris-Cl buffer (pH 8.0) at room temperature; single pass at control rate of 15lpm. (liters per min.) and collect filtrate which contains cholesterol oxidase. Store cholesterol oxidase (filtrate) solution at 5° C.

STEP 5

Cholesterol Oxidase Concentration and Dialysis

Maintain temperature of cholesterol oxidase solution reservoir at 5° C. and use an ultrafiltration membrane. Concentrate to 1/10 the volume. Dilute to original volume and concentrate to 60 units of cholesterol oxidase per ml.

EXAMPLE 2

Five thousand liters of fermentation beer, produced by bacteria in accordance with U.S. Pat. No. 3,909,359, is worked up as follows:

STEP 1

Filtration

Add 1% wt./vol. Standard Supercell as admix to beer, and using a rotary vacuum filter (Feinc), precoated with Celaton FW-6, filter the beer. Very gently agitate the beer plus filter aid during filtration.

STEP 2

Enzyme Release and Second Filtration

Combine cake from filtration (Step 1) with a surfactant solution composed of 750 liters of deionized water and 7.5 kg. of Triton X-100. Agitate for one hour. Precoat filter press with 50 kg. of Celaton FW-6, then filter and collect filtrate. Wash cake with 500 liters of deionized water in a single pass, combine with filtrate.

STEP 3

Surfactant Extraction and Ammonium Sulfate Precipitation

Precool precipitation filtrate obtained in Step 2 to 0° C. Precool 450 liters of $H_2O$ saturated n-butanol to 0° C. and combine with the precooled filtrate, maintaining temperature at 0° C. and begin agitation. Add 100 gm. of $(NH_4)_2SO_4$ per liter of filtrate, agitate for 60 minutes. Add 3 gm. of Standard Supercell as admix per liter of filtrate and allow to settle for 30 minutes.

Filter on press with 3 gm. of Celaton FW-6 per liter of filtrate as precoat. Blow press dry.

Be certain butanol and aqueous phases contain no precipitate before processing. Wash cake with 100 liters of $H_2O$ saturated n-butanol. Precooled to 0° C.; single pass (be certain wash contains no precipitate). Blow press dry. Elute press with 900 liters of 10 mM Tris-Cl buffer (pH 8.0) at room temperature; single pass at control rate of 15 lpm. and collect filtrate which contains cholesterol oxidase. Store cholesterol oxidase (filtrate) solution at 5° C.

STEP 4

Cholesterol Oxidase Concentration and Dialysis

Maintain temperature of cholesterol oxidase solution reservoir at 5° C. and use an ultrafiltration membrane. Concentrate to 1/10 the volume. Dilute to original volume and concentrate to 60 units of cholesterol oxidase per ml.

EXAMPLE 3

One liter of precooled (0° C.) methylene choloride is added to 2 liters of an aqueous processing solution containing cholesterol oxidase and a nonionic surfactant (Triton X-100) which has been precooled to 0° C. and begin agitation. Add 400 grams of $(NH_2)_2SO_4$; agitate for 30 minutes, maintaining temperature at 0° C., allow to settle for 30 minutes.

Filter and collect precipitate of cholesterol oxidase by conventional recovery techniques known by the art.

EXAMPLE 4

One liter of precooled (0° C.) n-butanol is added to 2 liters of an aqueous processing solution containing cholesterol oxidase and a nonionic surfactant (Triton DF-18) which has been precooled to 0° C. The solution is agitated, maintaining the temperature at 0° C. for 30 minutes. Allow to settle until aqueous phase and butanol phase separate. The nonionic surfactant is extracted into the butanol phase. The aqueous phase contains the cholesterol oxidase and the cholesterol oxidase is isolated from said aqueous phase by any conventional recovery techniques known by the art.

EXAMPLE 5

Ten liters of precooled (0° C.) water saturated n-butanol is added to one kilogram of a precipitate of cholesterol oxidase which contains a nonionic surfactant (Triton X-100). The mixture is agitated, maintaining the temperature at 0° C. for 30 minutes. The mixture is filtered and the cholesterol oxidase collected. The nonionic surfactant is extracted into the n-butanol.

EXAMPLE 6

One liter of precooled (0° C.) n-butanol is added to 2 liters of an aqueous processing solution containing cholesterol oxidase and a nonionic surfactant (Triton X-100) which has been precooled to 0° C. and begin agitation. Add 100 grams of $(NH_4)_2SO_4$; agitate for 30 minutes, maintaining temperature at 0° C., allow to settle for 30 minutes.

Filter and collect precipitate of cholesterol oxidase by conventional recovery techniques known by the art.

EXAMPLE 7

One liter of precooled (0° C.) n-butanol is added to 2 liters of an aqueous processing solution containing cholesterol oxidase and a nonionic surfactant (Triton X-100) which has been precooled to 0° C. and begin agitation. Add 600 grams of $(NH_4)_2SO_4$; agitate for 30 minutes, maintaining temperature at 0° C., allow to settle for 30 minutes.

Filter and collect precipitate of cholesterol oxidase by conventional recovery techniques known by the art.

The term "substantially free of nonionic surfactant" as used throughout the specification means cholesterol oxidase having less than one gram of nonionic surfactant per gram of protein. A cholesterol oxidase preparation having less than one gram of nonionic surfactant per gram of protein can be considered in the art to be substantially free of nonionic surfactant because cholesterol oxidase preparations prepared by prior isolation procedures utilizing a nonionic surfactant commonly contain nonionic surfactant in excess of one gram per gram of protein, for example preparations prepared by anionic exchange contain about 3 grams of nonionic surfactant per gram of protein.

I claim:

1. In a process of isolating cholesterol oxidase from an aqueous processing solution containing a nonionic surfactant, the improvement comprising removal of nonionic surfactant from said aqueous processing solution by contacting said aqueous processing solution with a water-immiscible solvent and precipitation of the cholesterol oxidase with an effective amount of a salt.

2. The improved method of claim 1 wherein said salt is selected from the group consisting of ammonium sulfate, magnesium sulfate, sodium sulfate and potassium sulfate.

3. The improved method of claim 2 wherein said extraction is accomplished with from about 0.1 to about 2 volumes of said water-immiscible solvent per volume of aqueous processing solution.

4. The improved method of claim 2 wherein said extraction is carried out at a temperature of between about −5° C. and about 5° C. and at a pH between about 4 and about 10.

5. The improved method of claim 2 wherein said water-immiscible solvent is n-butanol.

6. The improved method of claim 5 wherein said extraction is accomplished with from about 0.1 to about 2 volumes of n-butanol per volume of aqueous processing solution.

7. The improved method of claim 5 wherein said extraction is carried out at a temperature of between about −5° C. and about 5° C. and at a pH of between about 4 and about 10.

8. The improved method of claim 7 wherein said extraction is accomplished with from about 0.1 to about 2 volumes of n-butanol per volume of aqueous processing solution.

9. The improved method of claim 2 wherein said water immiscible solvent is methylene chloride.

10. A process for removing a nonionic surfactant and isolating cholesterol oxidase from an aqueous processing solution, which comprises extracting said nonionic surfactant with n-butanol and precipitation of the cholesterol oxidase with an effective amount of a salt selected from the group consisting of ammonium sulfate, magnesium sulfate, sodium sulfate and potassium sulfate.

11. The method according to claim 10 wherein the salt is ammonium sulfate.

12. The method according to claim 11 wherein said extraction is accomplished with from about 0.1 to about 2.0 volumes of n-butanol per volume of aqueous processing solution.

13. The method according to claim 12 wherein said extraction is carried out at a temperature of between about −5° C. and about 5° C.

14. The method according to claim 11 wherein said extraction is accomplish with from about 0.1 to about 2 volumes of n-butanol per volume of aqueous processing solution and the precipitation of cholesterol oxidase is accomplished with from about 50 to about 300 grams of ammonium sulfate per liter of aqueous processing solution.

15. The method according to claim 14 wherein said extraction and precipitation is carried out at a temperature of between about −5° C. and about 5° C.

16. In a process of isolating cholesterol oxidase from an aqueous processing solution containing a nonionic surfactant, the improvement comprising removal of nonionic surfactant from said aqueous processing solution by extraction with a water-immiscible solvent having a water solubility greater than 5% v/v.

17. The improved method of claim 16 wherein said extraction is accomplished with from about 0.1 to about 2 volumes of water-immiscible solvent having a water solubility of greater than 5% v/v.

18. The improved method of claim 16 wherein said extraction is carried out at a temperature of between about −5° C. and about 5° C. and at a pH of between about 4 and about 10.

19. The improved method of claim 16 wherein said water-immiscible solvent having a water solubility of greater than 5% v/v is n-butanol.

20. The improved method of claim 19 wherein said extraction is accomplished with from about 0.1 to about 2 volumes of n-butanol per volume of aqueous processing solution.

21. The improved method of claim 19 wherein said extraction is carried out at a temperature of between about −5° C. and about 5° C. and at a pH of between about 4 and about 10.

22. The improved method of claim 21 wherein said extraction is accomplished with from about 0.1 to about 2 volumes of n-butanol per volume of aqueous processing solution.

23. A process for removing nonionic surfactant from an aqueous processing solution containing cholesterol oxidase, which comprises extracting said nonionic surfactant with n-butanol.

24. The method according to claim 23 wherein said extraction is accomplished with from about 0.1 to about 2 volumes of n-butanol per volume of aqueous processing solution.

25. The method according to claim 23 wherein said extraction is carried out at a temperature of between about −5° C. and about 5° C. and at a pH of between about 4 and about 10.

26. The method according to claim 25 wherein said extraction is accomplished with from about 0.1 to about 2 volumes of n-butanol per volume of aqueous processing solution.

27. In a process of purifying a precipitate of cholesterol oxidase containing a nonionic surfactant, the improvement comprising removal of nonionic surfactant from said precipitate by extraction with a water-immiscible solvent.

28. The improved method of claim 27 wherein said extraction is accomplished with from about 3 to about 100 volumes per weight of precipitate.

29. The improved method of claim 27 wherein said extraction is carried out at a temperature of between about −5° C. and about 5° C. and at a pH of between about 4 and about 10.

30. The improved method of claim 27 wherein said water-immiscible solvent having a water solubility of greater than 5% v/v is n-butanol.

31. The improved method of claim 30 wherein said extraction is accomplished with from about 3 to about 100 volumes of n-butanol per weight of precipitate.

32. The improved method of claim 31 wherein said extraction is carried out at a temperature of between about −5° C. and about 5° C. and at a pH of between 4 and about 10.

33. A process for removing nonionic surfactant from a precipitate of cholesterol oxidase, which comprises extracting said nonionic surfactant with a water-immiscible solvent.

34. The method according to claim 33 wherein said extraction is accomplished with from about 3 to about 100 volumes per weight of precipitate.

35. The method according to claim 33 wherein said extraction is carried out at a temperature of between about −5° C. and about 5° C. and at a pH of between about 4 and about 10.

36. The method according to claim 33 wherein said water-immiscible solvent is n-butanol.

37. The method according to claim 36 wherein said extraction is accomplished with from about 3 to about 100 volumes of n-butanol per weight of precipitate.

38. The method according to claim 37 wherein said extrction is carried out at a temperature of between about −5° C. and about 5° C. and at a pH of between about 4 and about 10.

* * * * *